US008351569B2

(12) United States Patent
Baker

(10) Patent No.: US 8,351,569 B2
(45) Date of Patent: Jan. 8, 2013

(54) PHASE-SENSITIVE X-RAY IMAGER

(75) Inventor: Kevin Louis Baker, San Jose, CA (US)

(73) Assignee: Lawrence Livermore National Security, LLC, Livermore, CA (US)

(*) Notice: Subject to any disclaimer, the term of this patent is extended or adjusted under 35 U.S.C. 154(b) by 293 days.

(21) Appl. No.: 12/794,312

(22) Filed: Jun. 4, 2010

(65) Prior Publication Data

US 2010/0316190 A1 Dec. 16, 2010

Related U.S. Application Data

(60) Provisional application No. 61/186,635, filed on Jun. 12, 2009.

(51) Int. Cl.
*G01N 23/04* (2006.01)

(52) U.S. Cl. .......................................................... 378/62

(58) Field of Classification Search .................... 378/62
See application file for complete search history.

(56) References Cited

U.S. PATENT DOCUMENTS

| 7,869,567 | B2* | 1/2011 | Olivo et al. | 378/87 |
| 2003/0123611 | A1* | 7/2003 | Ohara et al. | 378/98.8 |
| 2006/0039532 | A1* | 2/2006 | Wu et al. | 378/62 |

* cited by examiner

*Primary Examiner* — Courtney Thomas
(74) *Attorney, Agent, or Firm* — John P. Wooldridge

(57) ABSTRACT

X-ray phase sensitive wave-front sensor techniques are detailed that are capable of measuring the entire two-dimensional x-ray electric field, both the amplitude and phase, with a single measurement. These Hartmann sensing and 2-D Shear interferometry wave-front sensors do not require a temporally coherent source and are therefore compatible with x-ray tubes and also with laser-produced or x-pinch x-ray sources.

26 Claims, 18 Drawing Sheets

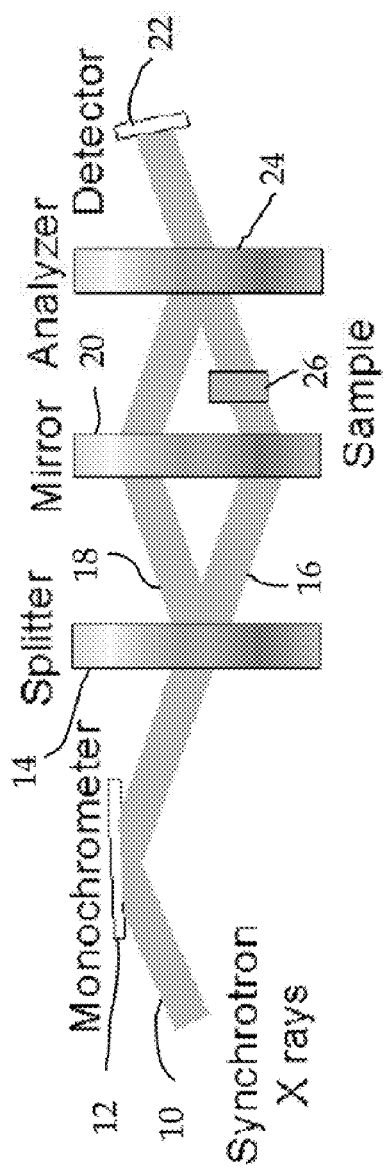
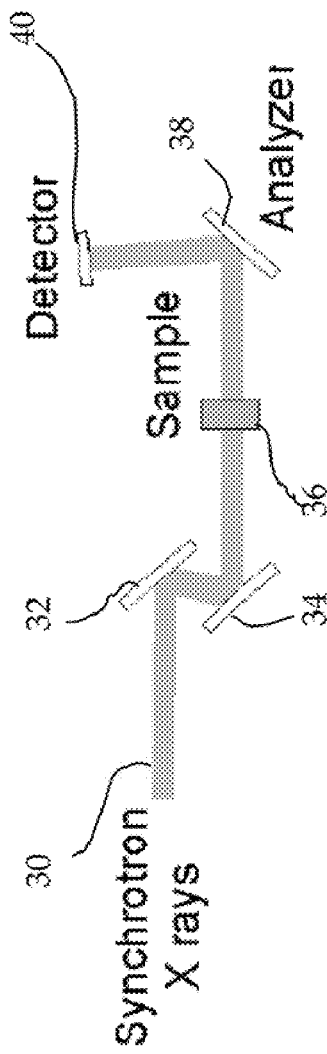
Figure 1A
(Prior art)
Figure 1B
(Prior art)

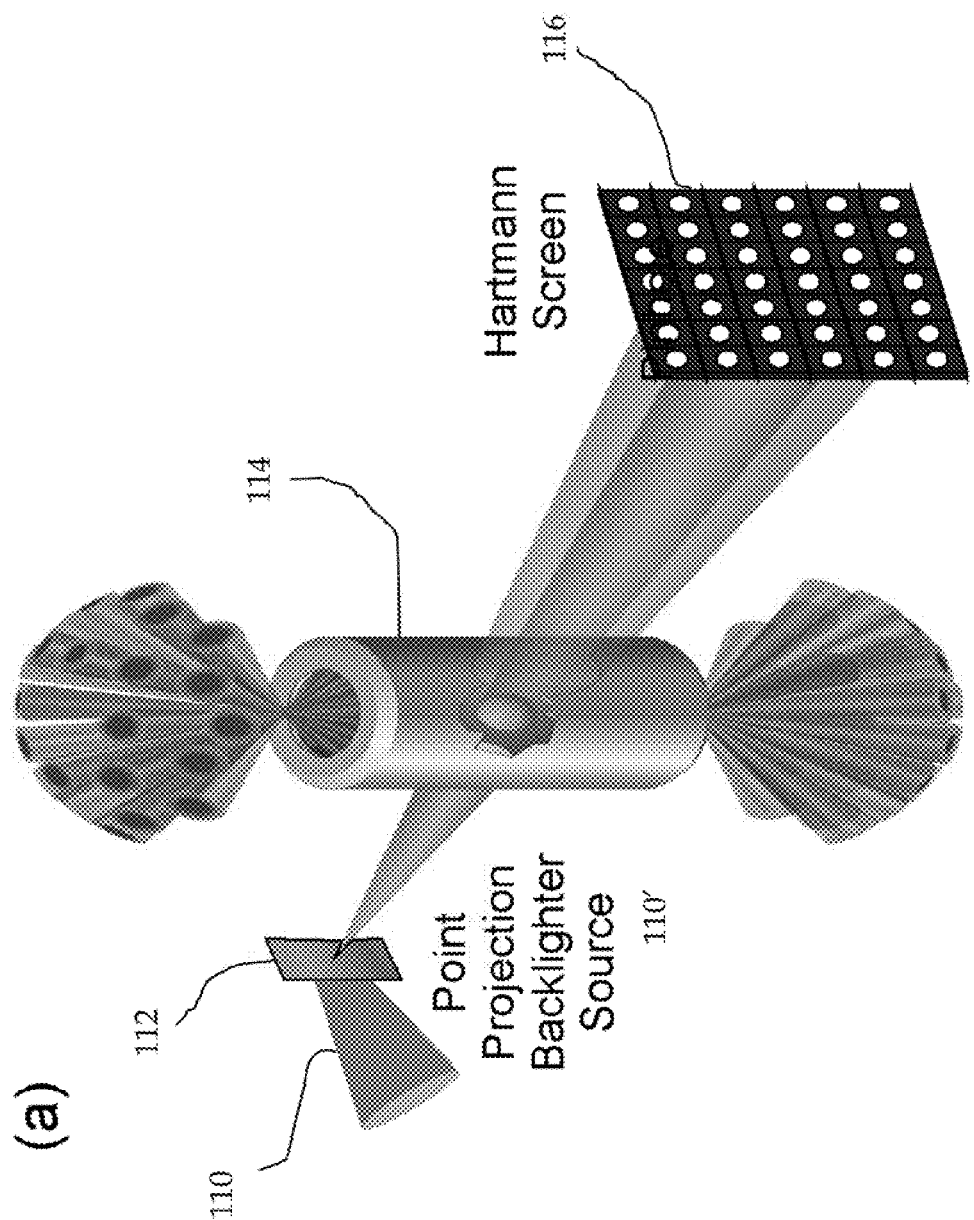

PHASE-SENSITIVE X-RAY IMAGER

CROSS-REFERENCE TO RELATED APPLICATIONS

This application claims the benefit of U.S. Provisional Patent Application No. 61/186,635 titled "Phase-Sensitive X-Ray Imager," filed Jun. 12, 2009, incorporated herein by reference.

STATEMENT REGARDING FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC.

BACKGROUND OF THE INVENTION

1. Field of the Invention

The present invention relates to x-ray diagnostics, and more specifically, it relates to techniques for utilizing x-rays to characterize a sample.

2. Description of Related Art

Excluding skin cancer, breast cancer accounts for one in every three cancer diagnoses in the United States. As the leading cause of death in women age 35-50 in the U.S., breast cancer is a major public health problem, with 1 in 8 women expected to be diagnosed sometime during their lives. The National Cancer Institute has therefore designated breast cancer as a top research priority. X-ray mammography, based on absorption contrast, is currently the primary technique for the screening of breast cancer. Absorption contrast works well in distinguishing between hard tissue, bones and teeth, and soft tissues. In mammography, however, there is a need to distinguish between different types of soft tissue representing the malignant tissue and the normal tissue. As a consequence conventional absorptive mammograms have a high false positive rate, as high as 19 in 20, with up to 15% of patients with tumors not displaying irregular radiographs. The passage of x rays through a sample can be described by a complex index of refraction, $n=1-\delta-i\beta$, where $\delta$ represents a phase shift and $\beta$ represents absorption. For x-ray energies of 15-25 keV, typical of mammograms, the phase shift term can be up to 1000 times the absorption term. As x rays pass through the sample, the different soft tissue results in different phase shifts, thereby causing distortion of the wave-front and refraction of the x rays. A phase sensitive approach, as opposed to a pure absorption technique, can result in a lower dose to the patient, by going to higher x-ray energies and can result in a significantly less false positive ratio as the diagnostic would directly measure the malignant tissue and have a significantly high sensitivity due to the three orders of magnitude higher phase shift term as opposed to the absorption term.

Conventional x-ray absorptive radiography is also used in a broad range of scientific areas including materials science, high energy density physics and Inertial Confinement Fusion (ICF) to name a few. In ICF, low Z materials are compressed to create the high density and temperature conditions necessary for fusion to occur. This is another area where contrast is difficult to achieve with conventional absorptive radiography. In high energy density physics experiments and non-destructive testing, phase sensitive diagnostics would enable the study of low Z material mixing and material/plasma interpenetration experiments without the need to add high Z elements for contrast, the presence of which can change the physical properties of the experiment through radiative cooling. As with mammography, the inherent disparity between the magnitude of the phase shift and absorptive terms would enable substantial increases in the sensitivity of these phase sensitive techniques over conventional absorptive radiography.

Several phase sensitive x-ray mammography systems have been proposed for providing a higher sensitivity, a lower rate of false positives and a lower x-ray dose to the patient than current devices. Techniques used in such systems include interferometry, diffraction-enhanced imaging, phase contrast imaging and Moire deflectometry. These techniques have been unsuccessful for a variety of reasons.

Several techniques have been ported over from the optical regime into the hard x-ray regime to enable phase-sensitive measurements. Current techniques for phase-sensitive x-ray imaging involve x-ray interferometry, diffraction enhanced imaging, phase contrast and Moire' deflectometry techniques. Each of these techniques has limitations which prevent their widespread use for quantitative phase-sensitive x-ray imaging. X-ray interferometry, shown in FIG. 1A, utilizes three crystals to separate and recombine two hard x-ray beams to form an interference pattern on a detector. Synchrotron produced x-rays 10 are redirected by a monochrometer 12 and then are separated by a splitter 14, which separates the beam into two beams 16 and 18, which are redirected by mirror 20 to an analyzer 22 which then directs the beam to a detector 24. A sample 26 is placed in beam 16. Interferometry with hard x rays requires high temporal and spatial coherence and a very bright source to overcome the inefficiency of the crystals. Such techniques must use synchrotron sources. In addition, this interferometer is constructed from a single silicon crystal which greatly limits the size of the sample that can be studied. Diffraction-enhanced imaging, as shown in FIG. 1B, utilizes the rocking curve of a crystal as a filtering technique. Synchrotron produced x-rays 30 are redirected by a first monochrometer 32 and a second monochrometer 34 through a sample 36 and then are directed by and analyzer 38 to a detector 40. To quantitatively reconstruct the phase of an object requires many measurements at different analyzer angles to provide measurements of the entire field. It also requires a bright source due to the inefficiency of the crystals used as the analyzer. Phase contrast techniques, as shown in FIG. 3C, operate by taking images of the illuminated object at multiple distances from the target and iteratively reconstructing the phase of the object numerically. This technique requires measurements at multiple distances to reconstruct the various spatial scales in the object and is therefore not suitable for single shot operation. In FIG. 1C, synchrotron or micro-focus produced x-rays 50 pass through a sample 52, and onto a detector 54. Moire' deflectometry, as shown in FIG. 1D, can only reconstruct the phase of the x-ray wave-front in one dimension. To reconstruct the full field would require multiple measurements, again inconsistent with single shot operation. In the figure, synchrotron or micro-focus produced x-rays 60 pass through a sample 62, a phase grating 64, an absorption grating 66 and onto a detector 68.

Practical phase sensitive mammography and x-ray diagnostic systems that overcome the problems inherent in prior art systems are desired.

SUMMARY OF THE INVENTION

It is an object of the present invention to provide practical phase sensitive x-ray sample diagnostic systems; other objects will be apparent based on the disclosure herein.

Two exemplary x-ray phase sensitive wave-front sensor techniques are detailed that are capable of measuring the entire two-dimensional x-ray electric field, both the amplitude and phase, with a single measurement. These Hartmann sensing and 2-D Shear interferometry wave-front sensors do not require a temporally coherent source and are therefore compatible with x-ray tubes and also with laser-produced or x-pinch x-ray sources.

The invention has a variety of uses, including phase-sensitive x-ray radiography for high energy density physics, an X-ray wave-front sensor, e.g., for the Linac Coherent Light Source, phase-sensitive x-ray radiography for non-destructive testing applications and phase-sensitive x-ray mammography, allowing for lower x-ray doses to the patients, significantly lower false-positives and inherent sensitivity advantages over conventional radiography which will lead to earlier detection of cancers.

The design and simulations of the expected performance of an exemplary two-dimensional x-ray shearing interferometer and an exemplary Hartmann sensor are provided. An exemplary interferometer uses crossed phase gratings in a single plane and is capable of operation over a wide range of x-ray energies by varying the grating material and thickness. Both wave-front sensors are insensitive to vibrations and, unlike Moire' deflectometers, recover the full two-dimensional phase profile of the x-ray beam rather than the gradient in only one dimension.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 1A shows the prior art x-ray phase-sensitive technique referred to as x-ray interferometry.

FIG. 1B shows the prior art x-ray phase-sensitive technique referred to as diffraction-enhanced imaging.

FIG. 2A represents a point projection geometry used to measure the phase and attenuation of an object illuminated by a spherically diverging x-ray beam, similar to an x-pinch or x-ray tube geometry.

DETAILED DESCRIPTION OF THE INVENTION

A need exists for an increase in the sensitivity of x-ray imaging diagnostics and to enable diagnostics that can quantitatively measure the density of low Z material without the requirement of adding high Z contrast producing material. An approach to this challenge is the use of phase sensing techniques as opposed to traditional absorptive techniques. In particular, a study of two x-ray wave-front sensing techniques, Hartmann sensing and 2-D shear interferometry, and exemplary implementations of these two techniques is provided. Both of these techniques are capable of measuring the entire two-dimensional x-ray electric field, both the amplitude and phase, with a single measurement. These wave-front sensors do not require a temporally coherent source and are therefore compatible with laser-produced x rays. An exemplary technique utilizes an existing micro-focus x-ray source at Lawrence Livermore National Laboratory (LLNL). In high energy density physics experiments these phase sensitive diagnostics enable the study of low Z material mixing and material/plasma interpenetration experiments without the need to add high Z elements for contrast, the presence of which can change the physical properties of the experiment through radiative cooling.

These new phase sensitive hard x-ray imaging technique are far easier to implement and provide superior results to current techniques. The evaluations provided herein include discussions of the implementations of the necessary algorithms that simulate the performance of these techniques under realistic Conditions, the design of the wave-front sensors to measure the absorption and phase shift of the x-rays, and the construction and testing of these techniques in the laboratory, to quantitatively reconstruct the phase and absorption profile of a test object.

Figure 1C:
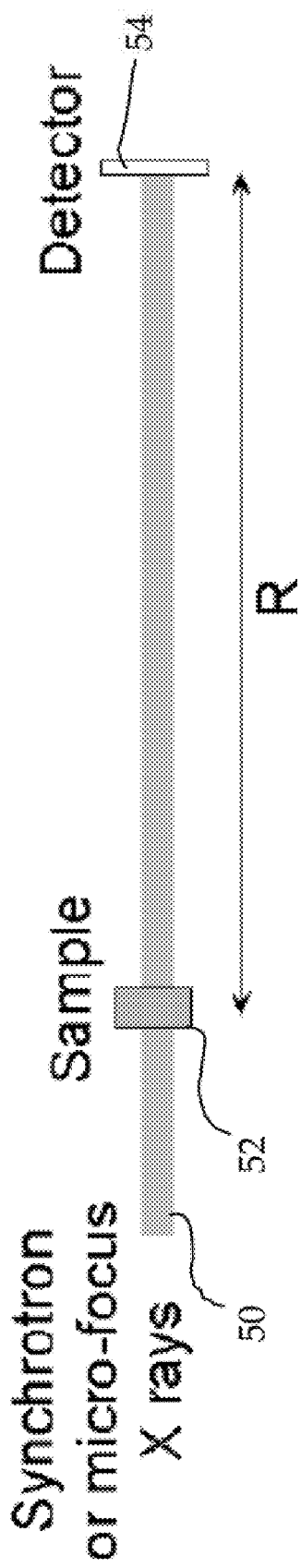
FIG. 1C shows the prior art x-ray phase-sensitive technique referred to as phase contrast.
Figure 1D:
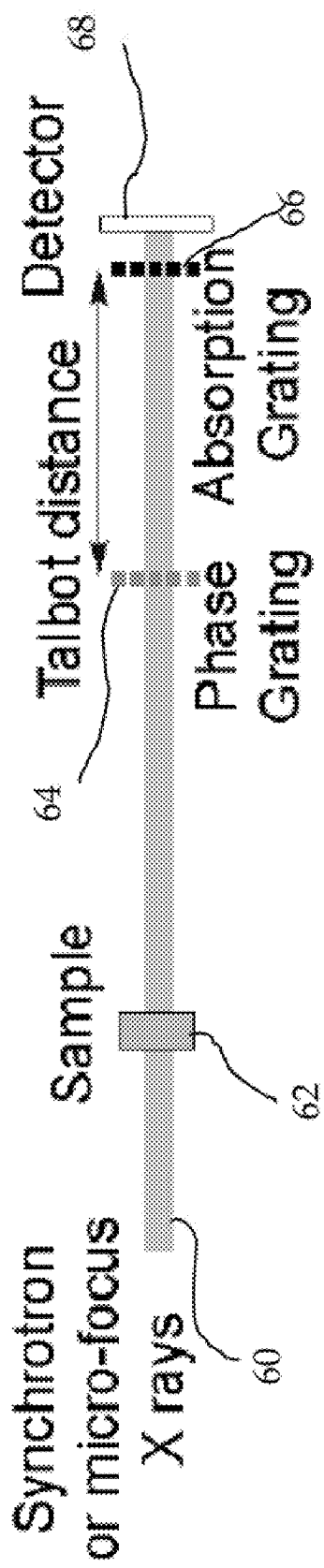
FIG. 1D shows the prior art x-ray phase-sensitive technique referred to as Moire' deflectometry.
Figure 1E:
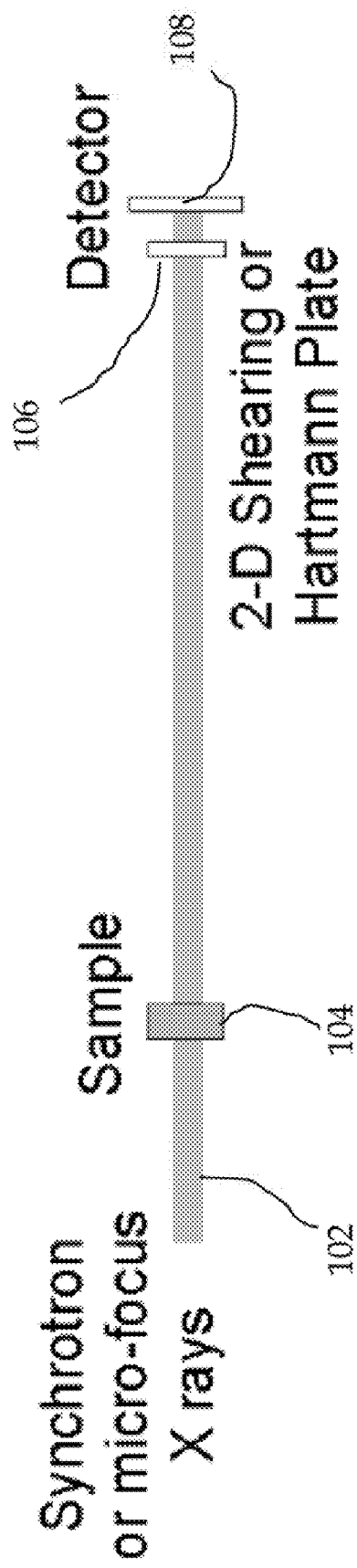
FIG. 1E shows a schematic of an exemplary embodiment of the present Hartmann and 2-D shear interferometry techniques.

FIG. 1E shows an example of both approaches. In the figure, an x-ray source, e.g., a synchrotron or a micro-focus tube, provides x-rays 102 that pass through a sample 104 and then a plate 106, e.g., a Hartmann plate or a 2-dimensional shearing plate, and then onto a detector 108.

Figure 2B:
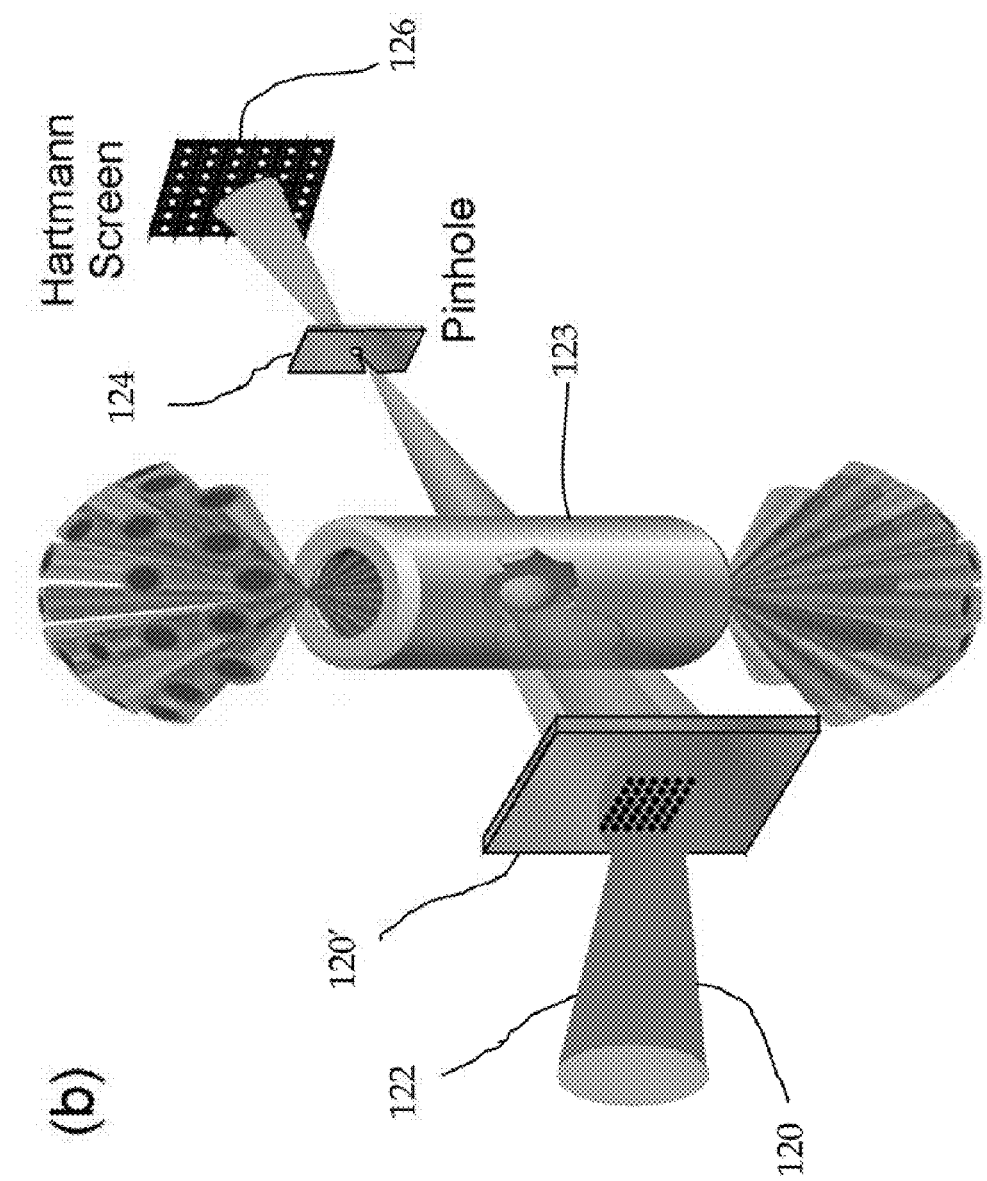
FIG. 2B shows a discreet area backlighter geometry in which the x-ray emitting material is localized on a grid pattern corresponding to the Hartmann screen or an array of pinholes is backlit, again corresponding to the Hartmann screen.

An example of the exemplary embodiments as they would be implemented on the NIF is shown in FIGS. 2A and 2B. FIG. 2A represents a point projection geometry, similar to an x-pinch or x-ray tube geometry. In the figure, a source (not shown), provides x-rays 110 which impinge onto a point projection backlighter source 112 which produces a diverging x-ray beam 110'. This diverging beam passes through the NIF target 114. The beam that exits the target continues to diverge and passes through a Hartmann screen 116 which produces a matrix of beamlets, according to the pattern of the screen 116, and the beamlets further propagate onto a detector (not shown). Although not an equivalent, a 2-D shearing plate can be substituted for the Hartmann screen. The two sensors are not equivalent at least because the Hartmann diagnostic is an amplitude mask and the shearing interferometer diagnostic is a phase mask.

FIG. 2B represents a discreet area backlighter geometry in which the x-ray emitting material is localized on a grid pattern corresponding to the Hartmann screen or an array of pinholes is backlit, again corresponding to the Hartmann screen. In FIG. 2B, an x-ray source (not shown) provides x-rays 120, which propagate onto a discreet area backlighter source 122, which provides a grid patterned (according to the geometry of the source 122) converging x-ray beam 120' that passes through target 123 and then a pinhole 124 before expanding and propagating through a Hartmann screen or shearing plate 126. In this case, either a low Z target material can be used to tamp the x-ray emitting grid pattern to prevent it from expanding or an array of pinholes can be backlit with an area x-ray backlighter. The detected beam is used to calculate the displacement and magnitude of the resultant array of x-ray spots. By measuring the amplitude of the spots, absorption information is recovered and by measuring the displacement of the spots, phase information is recovered. This technique enables reconstruction of the complete electromagnetic wave. This wave can then be propagated back to the phase object where image enhancement can occur through filtering of the angular spectrum of the x-rays. Both of the techniques, Hartmann sensing and shear interferometry, can utilize the same propagation and reconstruction algorithms and can be simulated using the same code, the only difference being a representation of an amplitude mask for the Hartmann diagnostic or a phase mask for the shearing interferometer diagnostic.

The prior art uses of related diagnostics have been in the visible regime and the phase is typically measured in a region where the beam is collimated. In the geometries envisioned for an application such as phase sensitive x-ray radiography of high energy density experiments, the beam will be spherically diverging at the place where the beam passes through the wavefront sensor. As such it will be necessary to measure a small phase shift on top of a largely spherical component representing the spherically diverging beam. To achieve this measurement, an iterative scheme to accomplish this task is provided. In a typical closed-loop adaptive optics application, an initial electric-field defined by a phase and amplitude enters an optical system and is relay imaged onto a deformable mirror and subsequently onto a wave-front sensor. In the case of a Hartmann or shearing interferometer wave-front sensor, an array of holes or a crossed transmission grating, respectively, is used to form spots on the wave-front sensor camera. The difference between the locations of these spots and a set of reference spots, which are generated when a nearly perfect wave-front propagates through the system without a sample, is used to determine the local gradients in the wave-front. The wave-front is then reconstructed from these local gradients. Wavefront reconstruction techniques are known in the art. In the prior art optical regime, through the use of a gain factor, a percentage of the reconstructed wave-front is used to change the shape of the deformable mirror such that the measured spots from subsequent measurements of the electric field approach the reference spot locations and hence the wave-front approaches a nearly perfect wave-front. In such closed-loop operation, small errors in the treatment of boundary conditions are mitigated by driving the phase to a flat wave-front.

Figure 3:
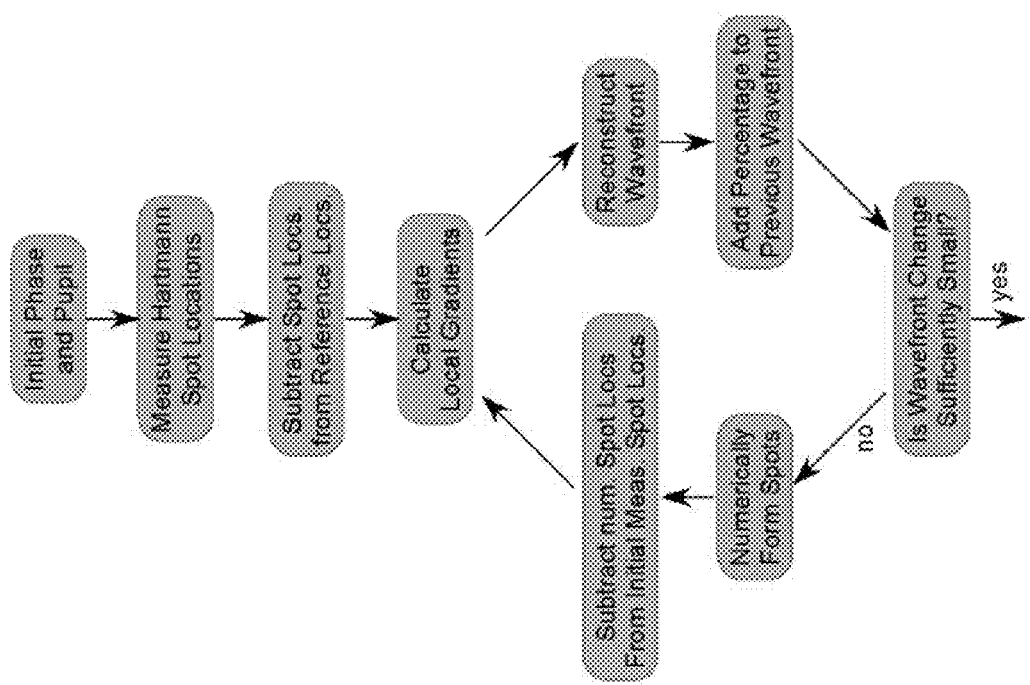
FIG. 3 shows an exemplary flowchart for the open-loop iterative algorithm.

For use in the present invention, to accurately reconstruct the phase using the present wave-front sensors with a spherically expanding beam, an iterative routine which is similar to the closed-loop adaptive optics system described above has been developed. A flow chart of an exemplary algorithm is shown below in FIG. 3. The primary difference between the closed-loop application described above and the exemplary iterative reconstruction process utilized in the present invention is that rather than driving the solution to the reference centroid locations with the use of a deformable mirror, the phase is driven to the initial measured centroid locations using a simulation loop. This is accomplished numerically by using the reconstructed phase to form simulated Hartmann spots on a simulated wave-front sensor camera and then comparing the numerically formed spots to the initial measured reference spots. These reference spots could also be taken offline using a micro-focus x-ray source without requiring additional shots at chamber center and without incurring damage to the amplitude/phase mask. The gradients are then calculated from the differences between the simulated spot locations and the measured spot locations. Although the initial measured spots contain detector noise, no noise will be added to the simulated Hartmann spots. The wave-front is reconstructed from these gradients and a numeric gain factor is used to add a percentage of the reconstructed wave-front to the composite wave-front from the previous iterations. In this approach the simulated Hartmann spot locations are driven towards the measured spot locations and hence the reconstructed wave-front is driven to the initial wave-front being measured. Using this technique, errors in the boundary conditions and nonlinearities can be significantly reduced, allowing large aberrations to be reconstructed with very low phase variance between the actual phase and the reconstructed phase. The iterative algorithm discussed above will lead to more accurate reconstructed wave-fronts and therefore greater sensitivity in the diagnostic. Preliminary studies of this algorithm have been implemented. These studies indicate that this algorithm can indeed be used to quantitatively reconstruct a large phase aberration or more importantly a small phase aberration on top of a large spherical component due to the expanding x-ray beam The essential components for these two wave-front sensors are (i) a Hartmann plate or screen for the Hartmann wave-front sensor or (ii) a crossed transmission phase grating structure for the shearing interferometer. Conceptually, the Hartmann screen is simply an array of holes which allow the x-rays to be transmitted as they pass through the holes and are attenuated by the plate elsewhere. As such the detector placed after the Hartmann plate measures a regular array of points corresponding to the hole pattern of the Hartmann plate. Exemplary technologies for producing these structures include laser machining and deep reactive ion etching. The Hartmann sensor is purely a ray tracing diagnostic and does not rely on interference to determine the phase. As such the spatial coherency requirements on the source are greatly reduced over that of the shearing interferometer given below.

The sensitivity expected from a Hartmann sensor can be calculated analytically as $$\sigma_{0\text{-}H} \approx \frac{\pi}{8}\left(\frac{\theta}{SNR}\right) = \frac{\pi}{8}\left(\frac{D}{L}\right)\left(\frac{1}{SNR}\right), \quad (1$$

where θ is the angular extent of the source, D is the source spot size, L is the distance between the source and the Hartmann sensor and SNR is the signal-to-noise-ratio of the measurement. For an x-ray spot size of 20 microns, a distance between the x-ray source and the Hartmann screen of 20 cm and an SNR of 20, one would expect to measure angular deflections of θ~2 μrad. For a pitch, p, on the Hartmann screen of 20 microns and an x-ray wavelength of ~2 angstroms, this would represent a detection of a phase change, φ, across the 20 μm pitch of φ=2πp θ/λ~1.3 radians. From FIG. 4A, at ~5 keV, the distance over which x-rays experience a π phase shift in a low Z material such as Beryllium is a factor of 100 times smaller than the distance over which they experience a 1/e absorption depth. This discrepancy is even larger in Hydrogen, Deuterium, Tritium and Helium, approaching a value of 1000, at this energy range and at higher energies of 15-25 keV even elements as high as Carbon display a factor of 1000 difference in the 1/e absorption length versus a π phase shift length. As such, phase sensitive diagnostics can provide a much higher sensitivity than current absorptive diagnostics over these energy ranges and element atomic numbers.

Figure 4A:
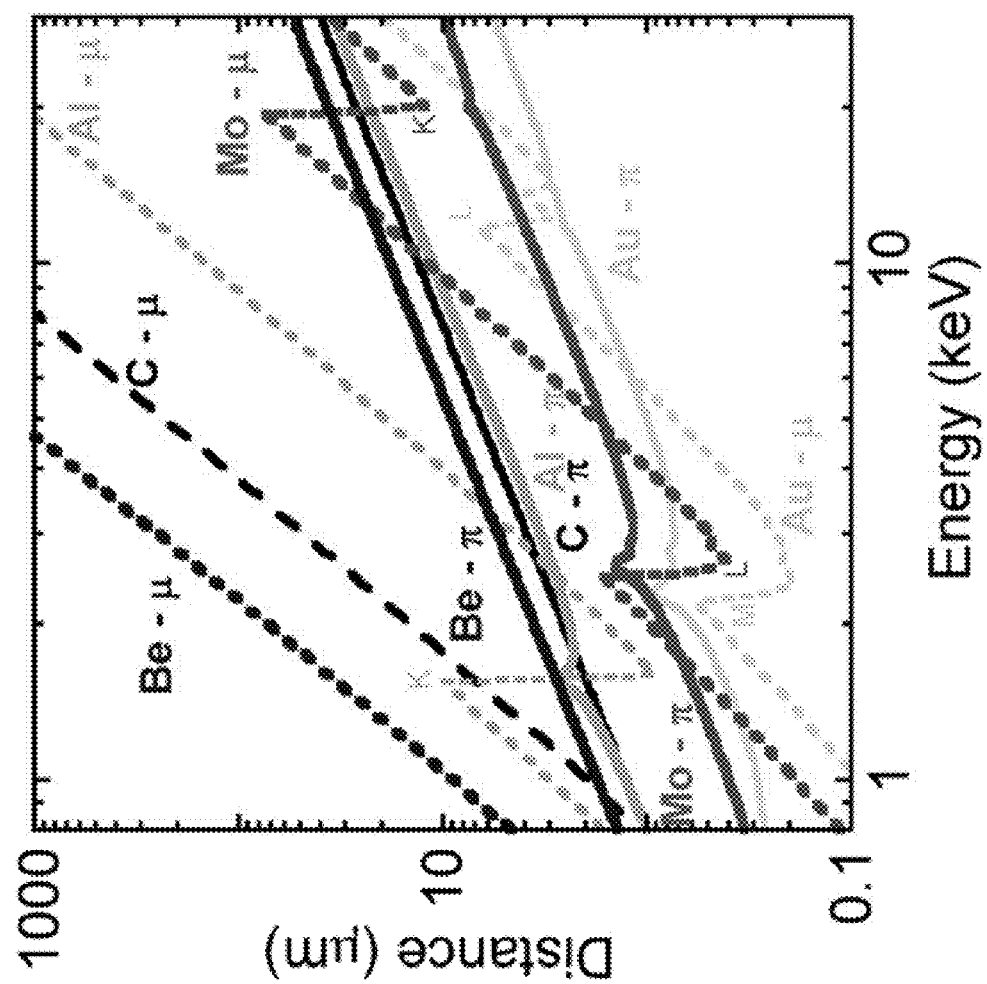
FIG. 4A shows the $\pi$ phase shift and $1/e$ absorption lengths for several elements as a function of x-ray energy is shown in as solid and dashed lines of the same color, respectively.
Figure 4B:
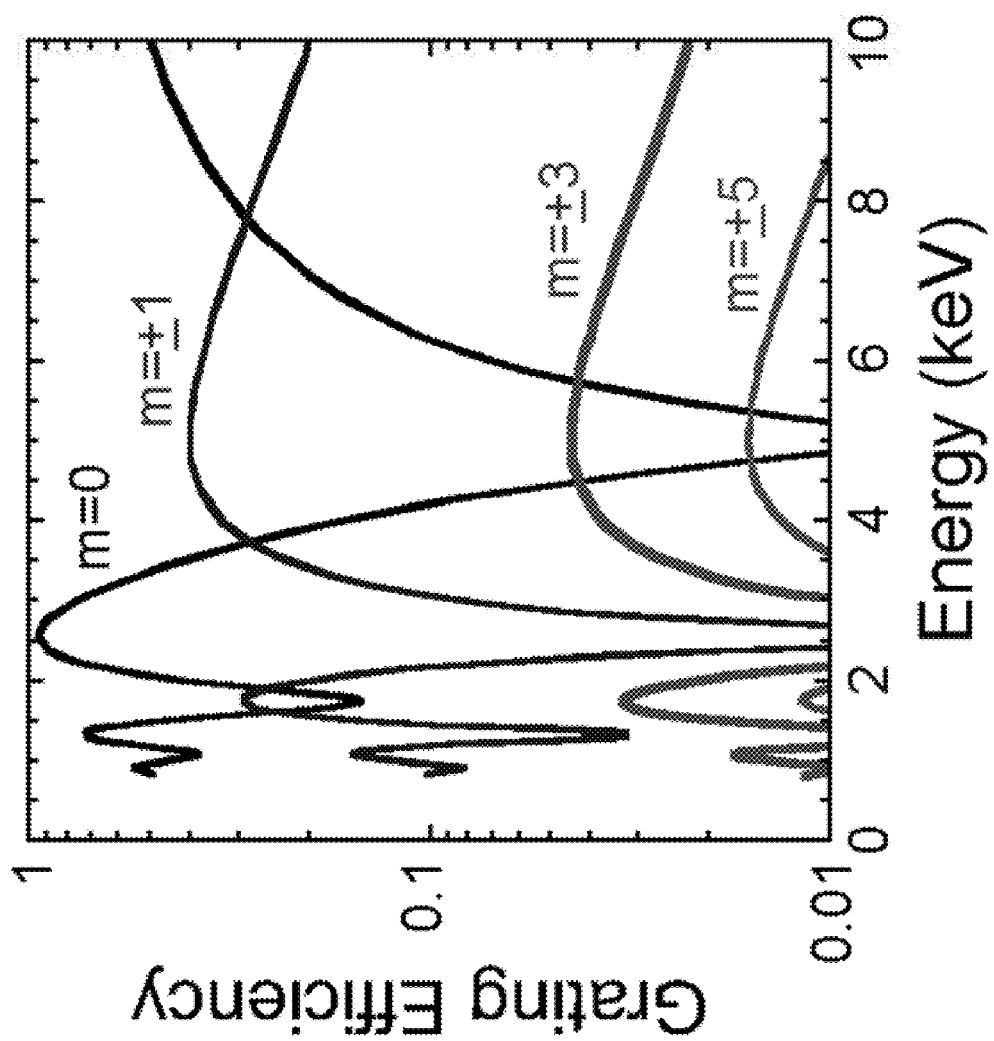
FIG. 4B shows the efficiency of the different orders for a transmission grating composed of carbon.

The crossed phase grating of the invention produces intensity spots on the detector whose relative shifts determine the local wave-front gradient very similar to the Hartmann wave-front sensor discussed above. When a periodic structure is placed in a beam, images of that structure will appear downstream of the object. More precisely, if a phase grating is placed in the beam, where the grating is composed of alternating equal width bars of 0 and $\pi$ phases, then the field at the location of the phase structure will be reproduced a distance $d_T=d^2/2\lambda$ downstream of the phase structure, as well as multiples of this distance. In this expression, $d_T$ is the Talbot distance, d represents the pitch of the phase grating and $\lambda$ is the wavelength of the source. At a distance equal to $d_T/4$ and $3d_T/4$, the initial phase pattern across the beam has become uniform and the initially uniform intensity has acquired the periodic structure of the initial phase pattern with the pitch of the intensity pattern equal to half that of the original phase grating. At a distance of $d_T/2$, the phase pattern is reversed from the original phase grating and the intensity pattern is uniform such that this particular location cannot be used for wave-front sensing. In practice, the intensity pattern has well defined spots for propagation distances between $d_T/16$ and $7d_T/16$ and between $9d_T/16$ and $15d_T/16$. Each of the exemplary two orthogonal gratings is designed such that the even orders of the grating are eliminated. In order for the efficiency of the even orders, greater than the m=0 order, of a transmission grating to go to zero at x-ray wavelengths, the width of the slits must be half of the grating pitch. In addition, for the efficiency of the m=0 order of the grating to go to zero, there must be negligible absorption and the bar structure of the grating must produce a shift of $\pi$ radians relative to the slits of the grating. At x-ray wavelengths, the index of refraction is expressed as $n=(1-\delta)+i\beta$, where $1-\delta$ gives rise to a phase shift as the x-rays pass through the sample and the $\beta$ term results in absorption. The length for a $\pi$ phase shift, $x_\mu$, can be expressed as $x_\mu=\lambda/(2\delta)$ and the absorption length, $x_\mu$, can be written as $x_\mu=\lambda/(4\pi\beta)$. FIGS. 4A and 4B represent the attenuation and $\pi$ phase shift lengths for several elements as a function of x-ray energy. As can be seen in FIGS. 4A and 4B, the light elements can easily be made to provide the desired $\pi$ phase shift and yet result in negligible absorption of the x rays. Photolithography etching and electroplating and bulk assembly and polishing, e.g., are usable to produce these structures. The $\pi$ phase shift and 1/e absorption lengths for several elements as a function of x-ray energy is shown in FIG. 4A as solid and dashed lines of the same color, respectively. The efficiency of the different orders for a transmission grating composed of carbon is shown in FIG. 4B. The transmission grating has been designed such that the even orders higher than the 0'th order have no energy and that the m=0 order approaches 0 at the design wavelength of 5 keV.

The coherency requirements for the shearing interferometer are such that the source is required to be nearly spatially coherent. This is consistent with using a laser-produced, x-pinch or micro-focus x-ray source in the geometry shown in FIGS. 2A and 2B. The pinhole shown in front of the x-ray source should ideally be sufficiently small that the diffractive spreading of the x rays exceeds the pitch of the gratings or $L\lambda/D>p$, where L is the distance between the source and the grating, $\lambda$ is the wavelength, D is the diameter of the x-ray source and p is the pitch of the grating. For a grating pitch of p=4 microns, an x-ray wavelength of $\lambda=2$ angstroms and a separation of L=20 cm between the x-ray source and the crossed phase grating, the requirements on the pinhole size are that it be less than D~10 microns in size. By proper spacing of an array of pinholes in front of the x-ray source, the fringes formed behind the crossed phase grating from each of the pinholes can be made to overlap creating a periodic backlighter. In that case a broad area source can be utilized, thereby decoupling the spatial coherence of the sources from the total source size. Therefore the flux can be increased without destroying the fringe visibility on the detector.

Both simulations discussed next utilize wave optics simulations to transport the electric field between the various planes. The grating structure and the phase object are added to the electric field after the field has been propagated to its respective location. The wavefront is reconstructed from the simulated spots by first locating the displacement of each of the spots with a center-of-mass centroider, and then reconstructing the resulting gradients with a multigrid wavefront reconstructor.

Reconstruction of the Far-Field Intensity Pattern

Figure 5A:
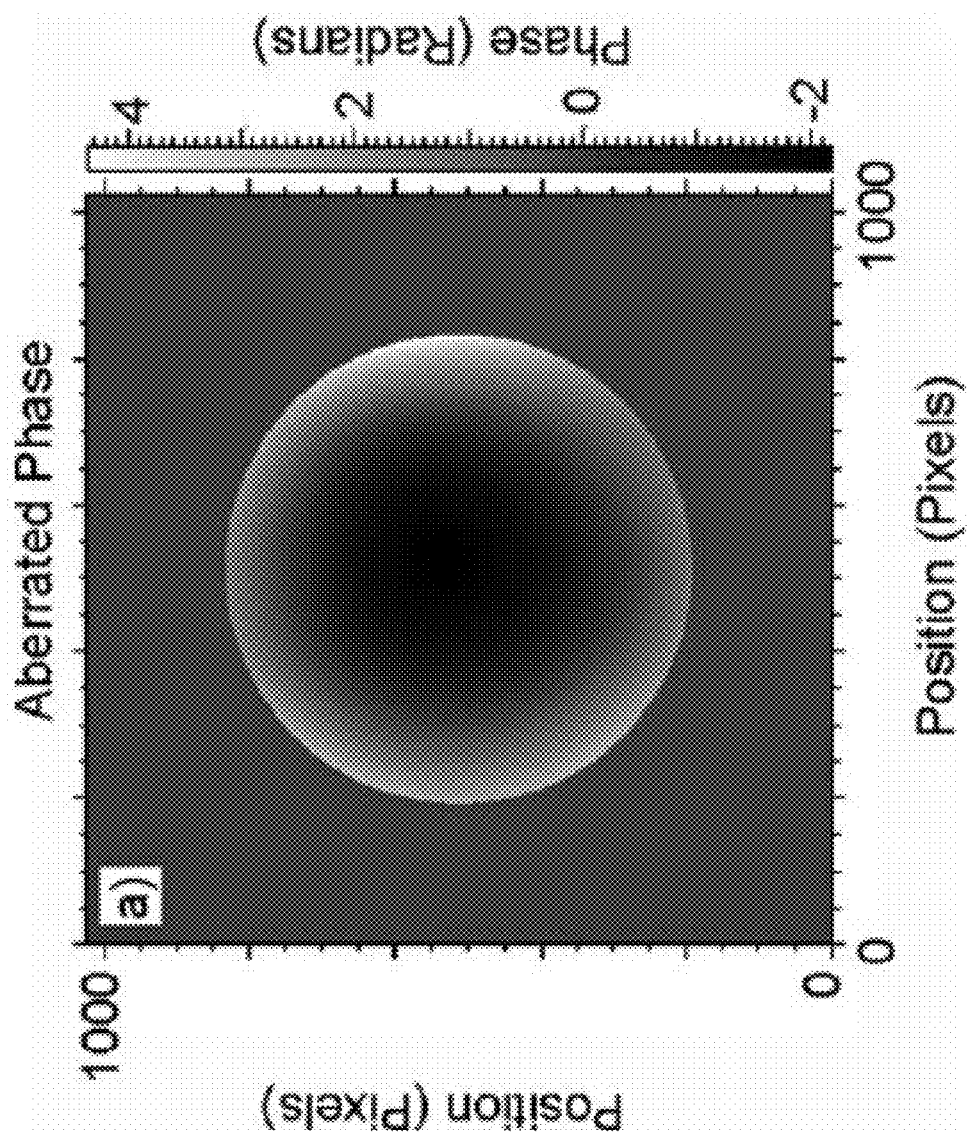
FIGS. 5A-C show reconstructed far-field spot using the shearing interferometer.
Figure 5B:
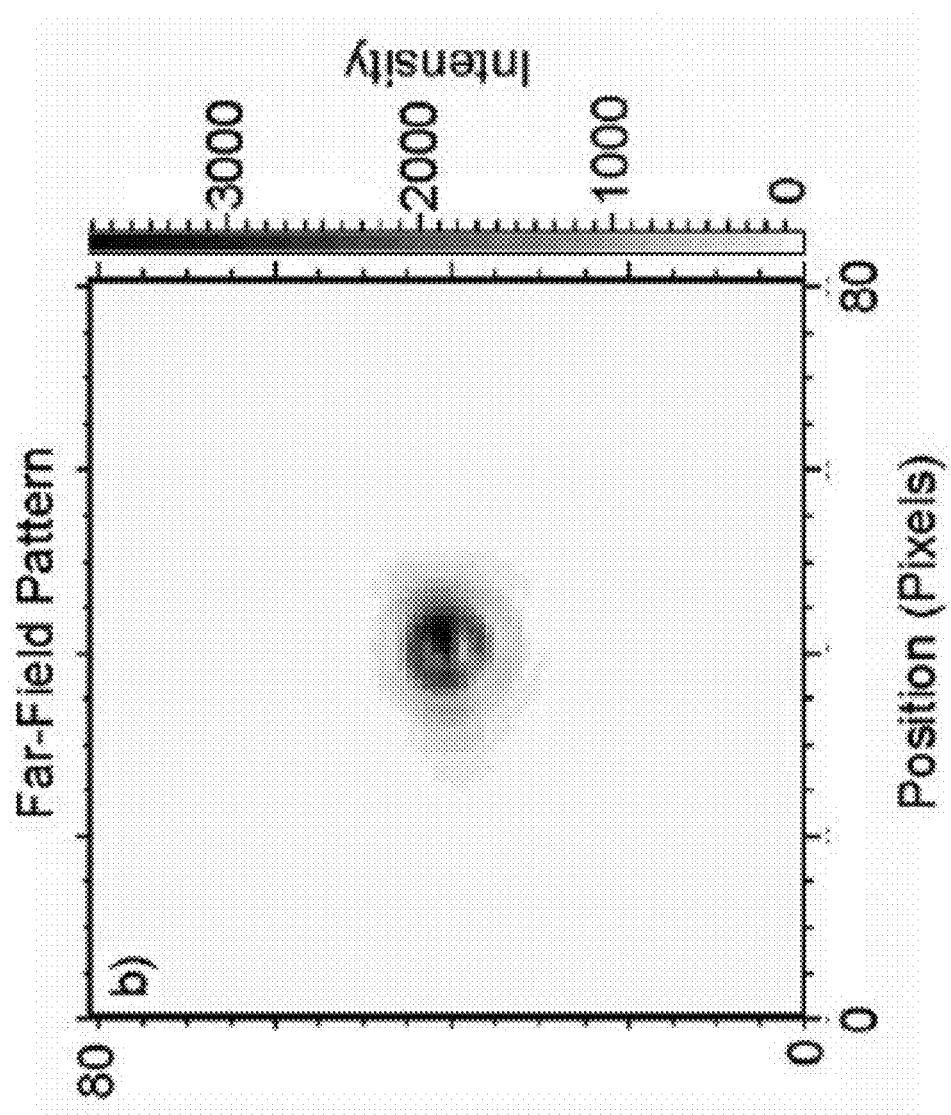
Figure 5C:
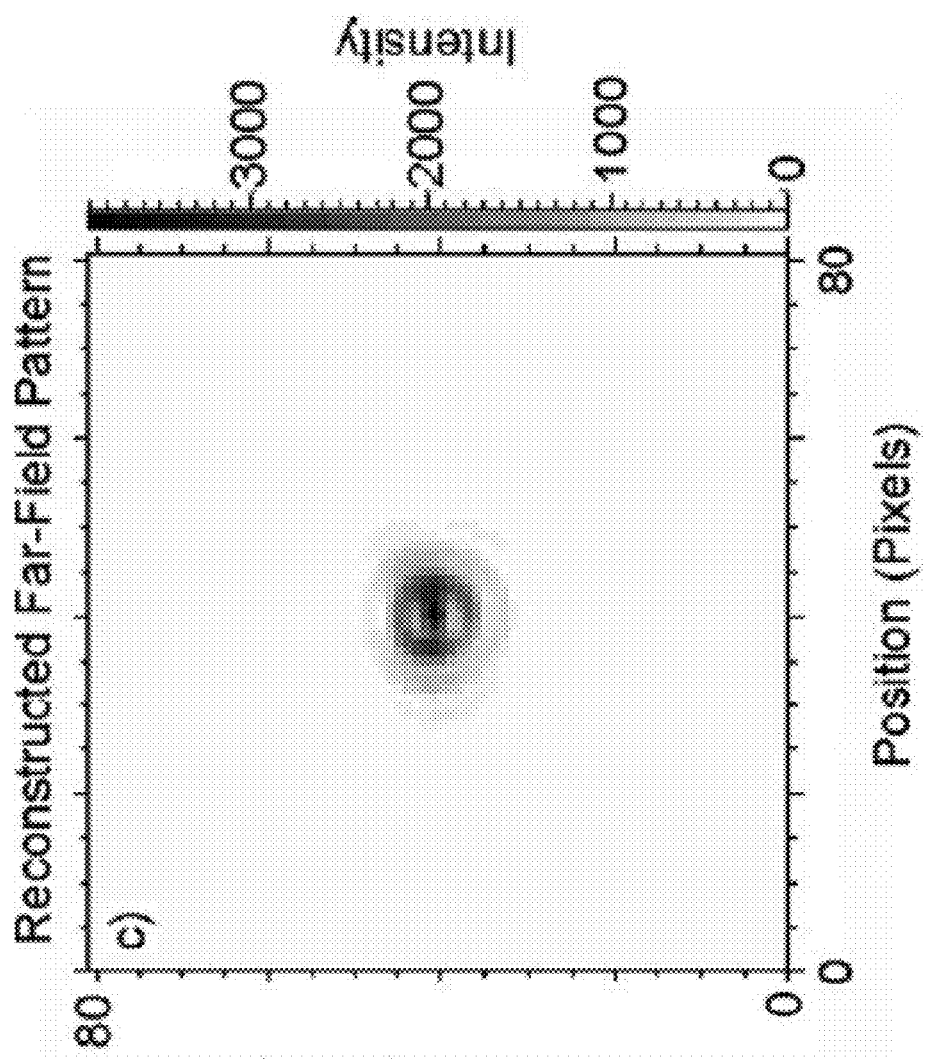

The first application is motivated by the desire to know the far-field intensity pattern that is being used to scatter off molecules in an attempt to characterize the structure of protein molecules that are not easily grown as crystals. The protein structure is determined by measuring the diffraction pattern from single molecules many times to build up all orientations of the molecules, and then through tomographic reconstruction techniques to recover the protein's 3-D structure. In this case, the x-ray beam is focused and the shearing interferometer is placed 3 meters downstream of focus. The beam propagates 15 mm past the phase gratings where the resultant spots are formed on the detector. The intensity of the spots provides the local intensity of the field, and the displacement of the spots determines the phase of the field at the phase gratings. The reconstructed field is then propagated back to focus to recover the far-field pattern of the x-ray beam. For this application, an initial phase aberration was placed on the x-ray beam as shown in FIG. 5A. The resultant far-field pattern with that phase aberration is shown in FIG. 5B. After the phase of the beam has been determined by reconstructing the local gradients from the spot displacements, the field is back-propagated to focus where the far-field intensity pattern is formed, as shown in FIG. 5C.

Reconstruction of a Phase Object

Figure 6A:
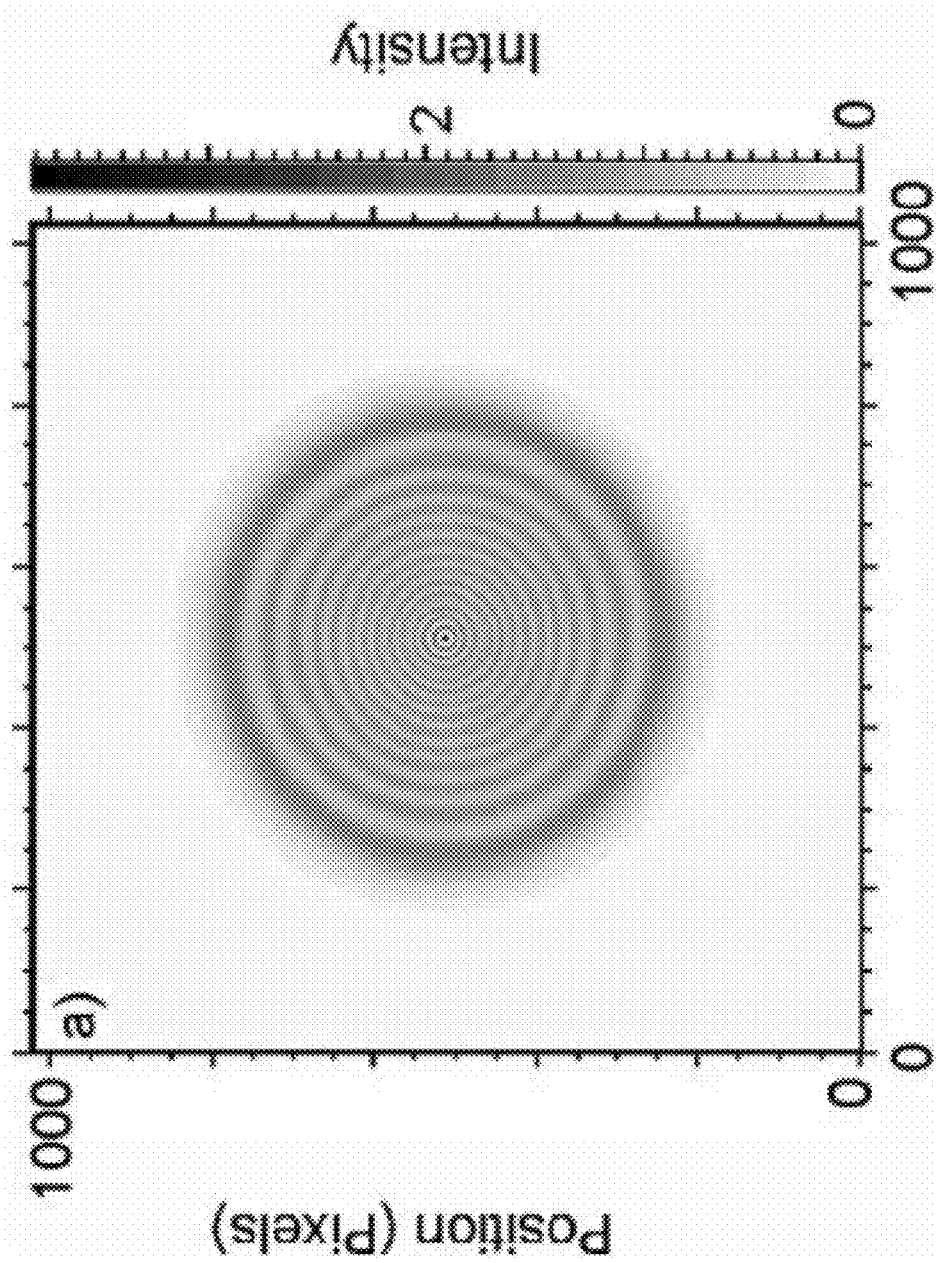
FIGS. 6A-D show intensity profiles at the entrance and 15 mm after having passed through a 2-D crossed phase grating.
Figure 6B:
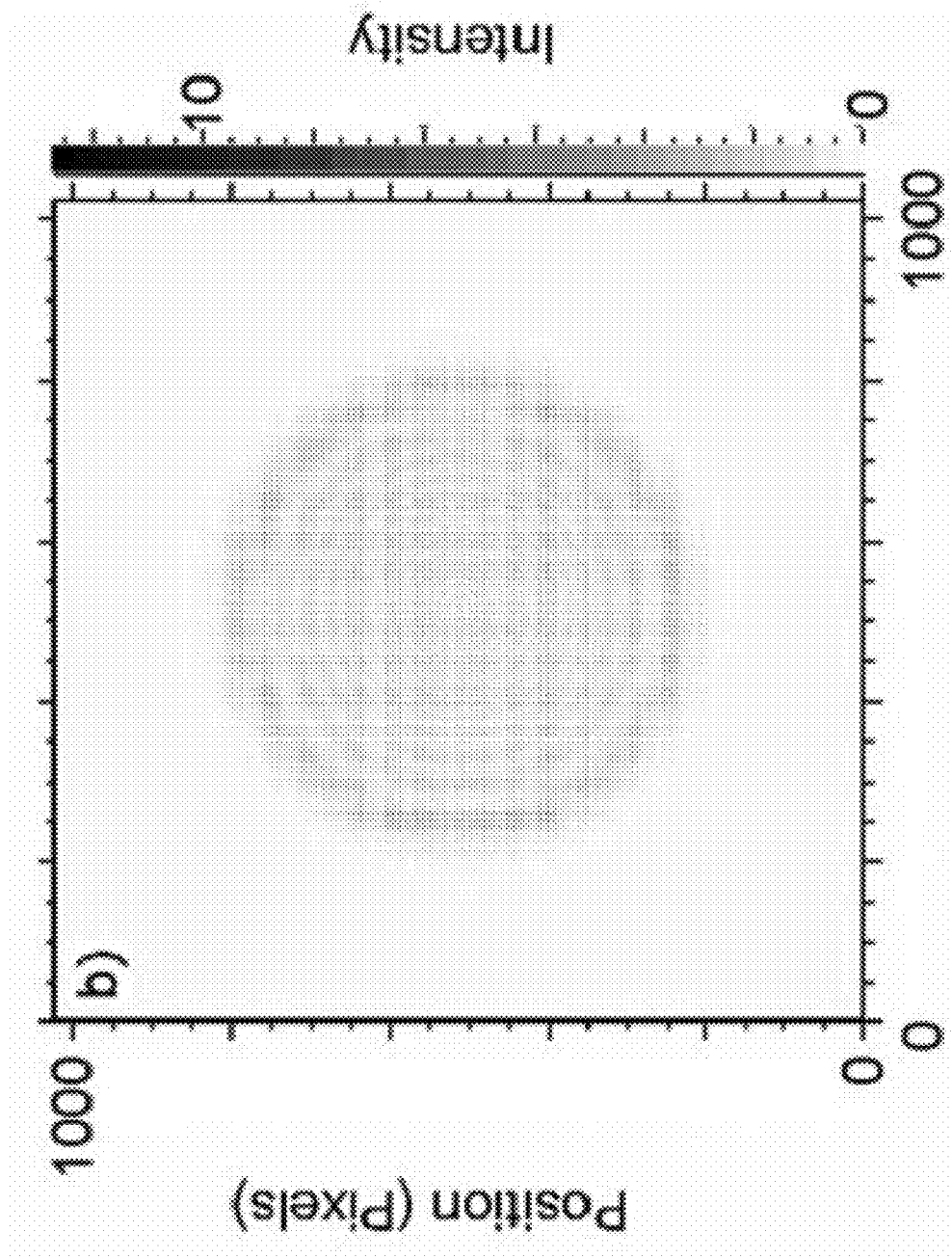
Figure 6C:
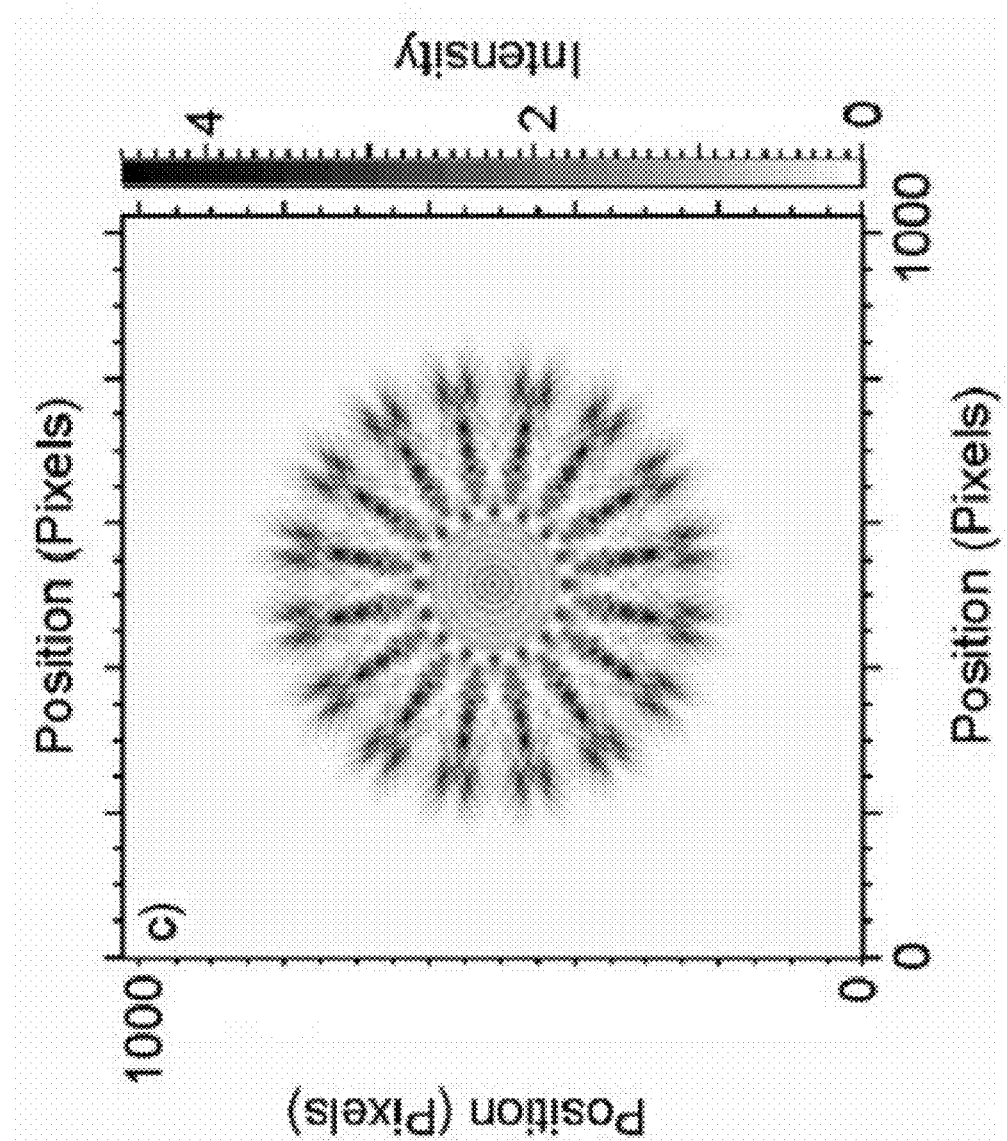
Figure 6D:
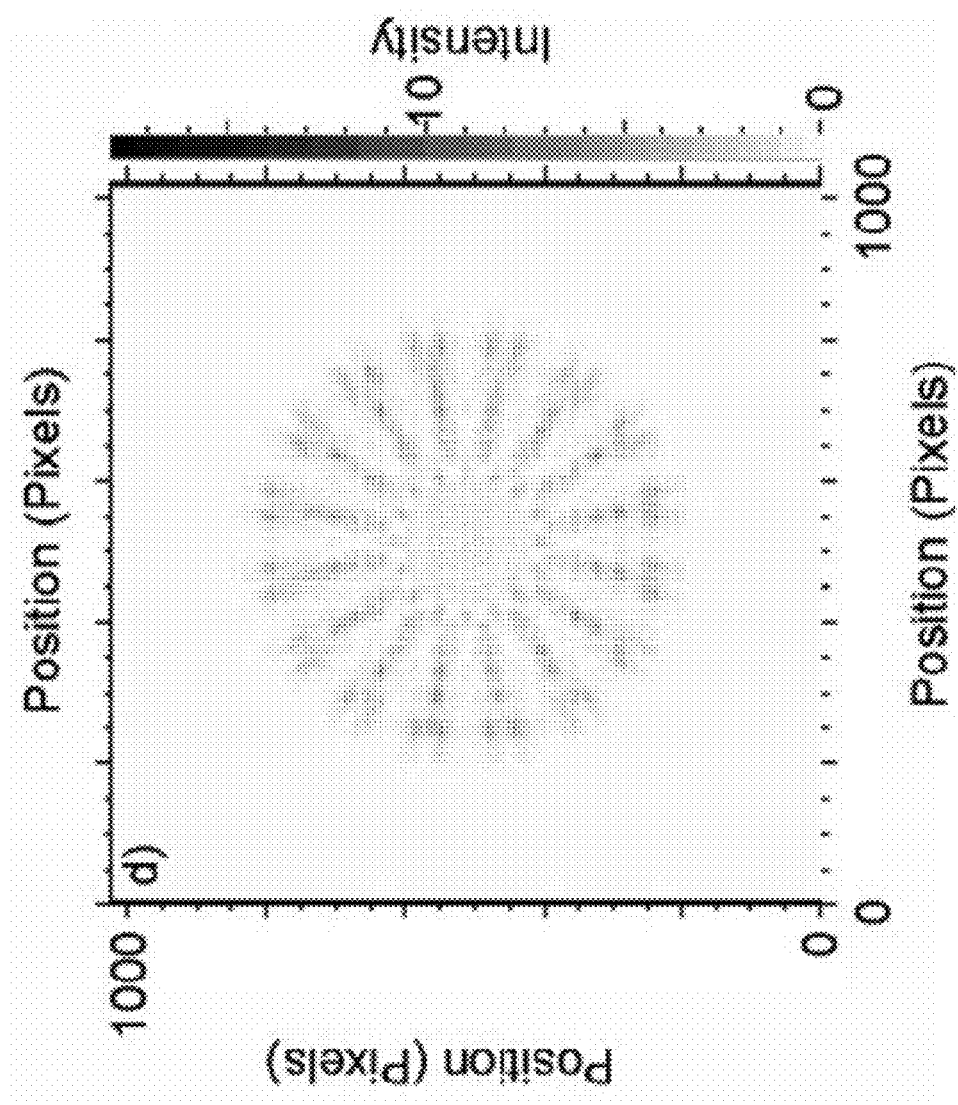
Figure 7A:
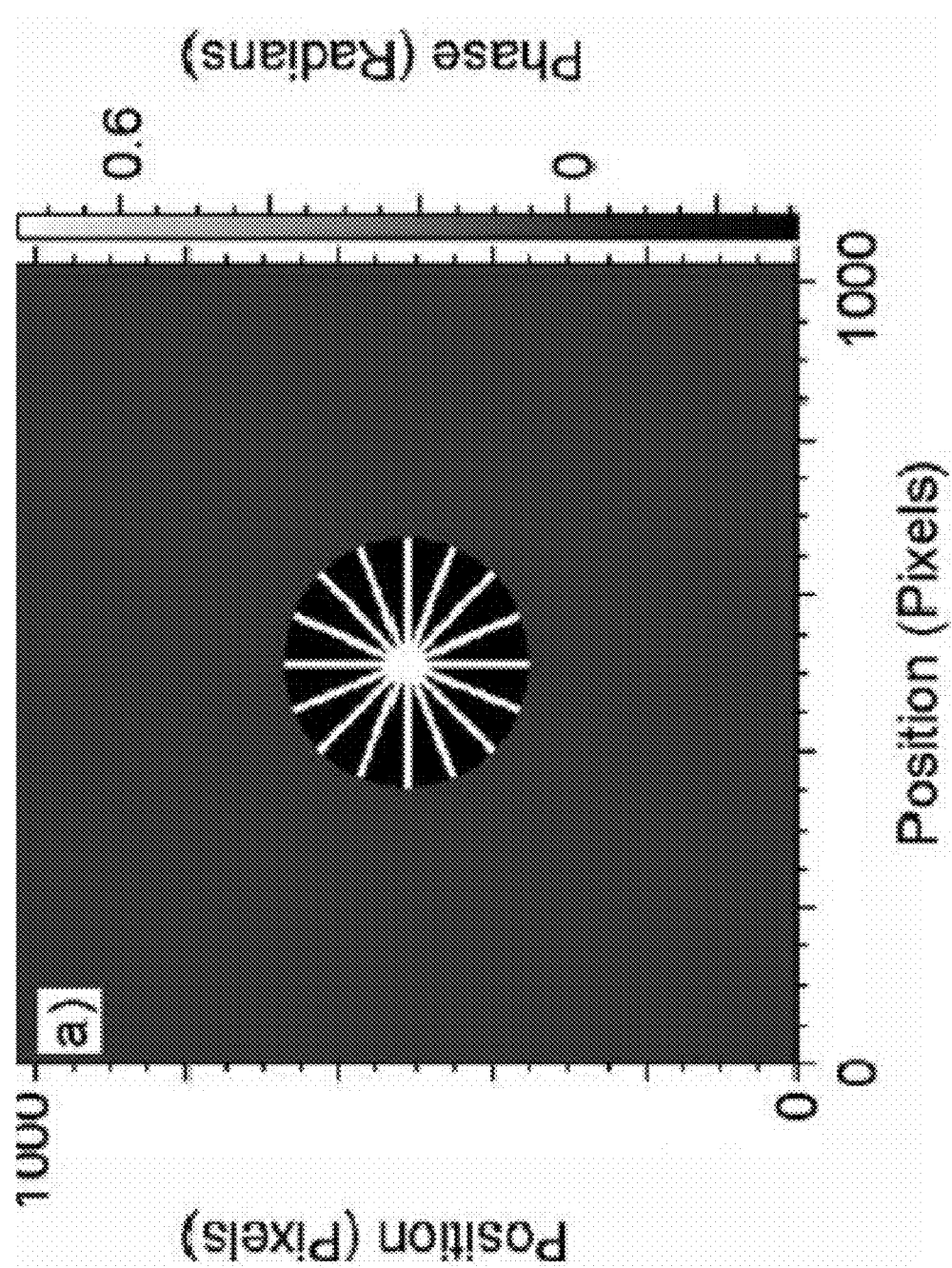
FIG. 7A show the actual phase of the object placed in the expanding x-ray beam.
Figure 7B:
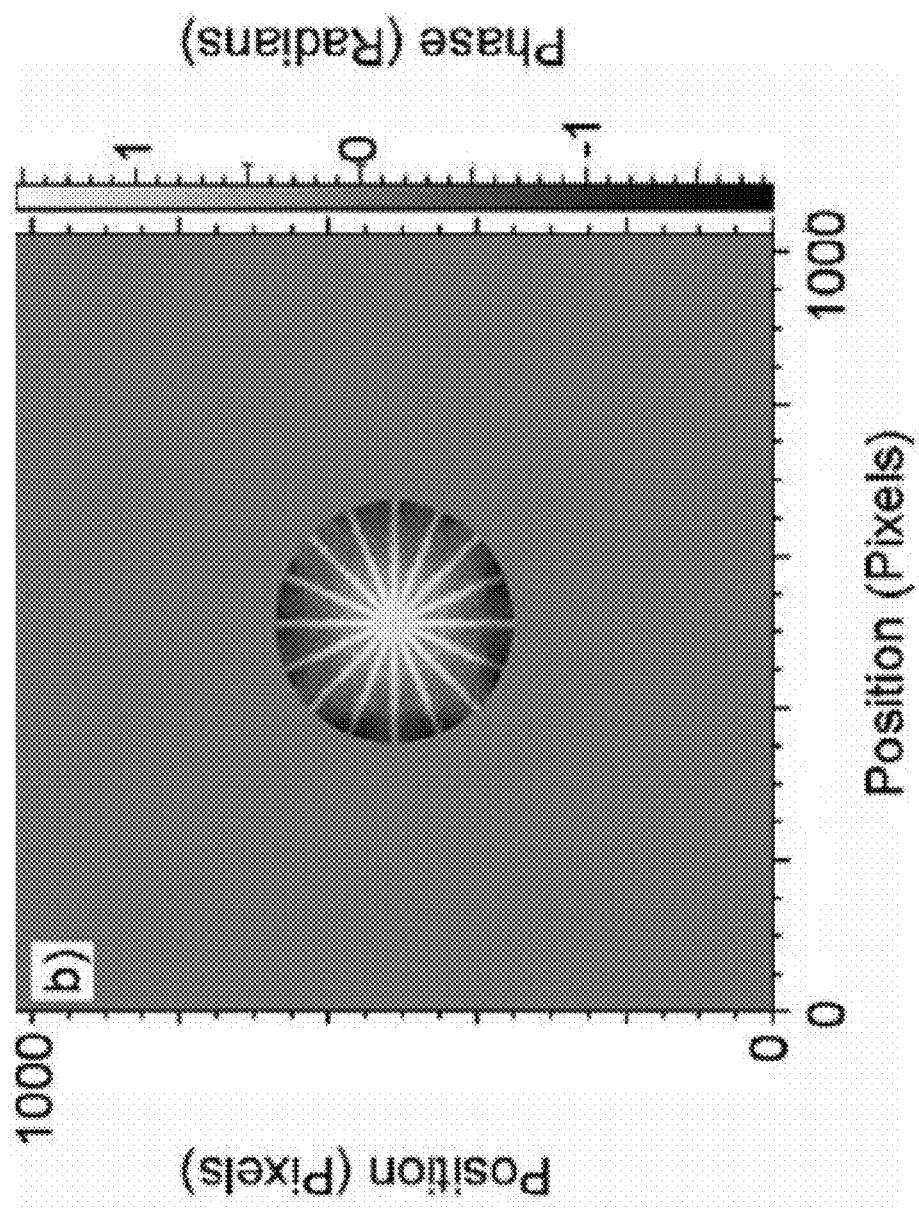
FIG. 7B shows the reconstructed phase.
Figure 7C:
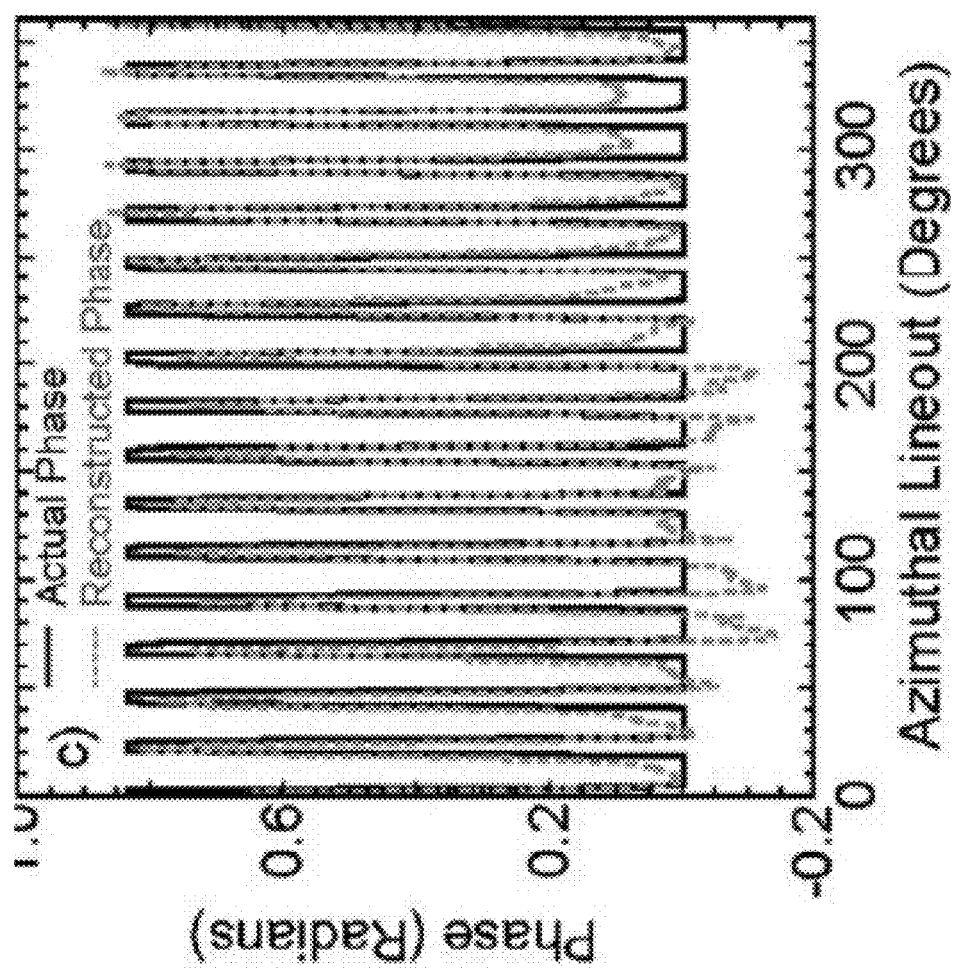
FIG. 7C shows an azimuthal lineout through the two phases at a radius of one fourth the object's diameter.

The second application involves using an x-ray source to determine the phase of an unknown object placed in the beam. This application is also done with an expanding beam, which is much more difficult than a collimated beam due to the large focus term that dominates the phase measurement. In this case, a star-shaped phase object is placed midway between the focus of the x-ray beam and the crossed phase gratings. FIGS. 6A and 6B represent the intensity pattern at the crossed phase gratings and 15 mm past the crossed phase gratings, respectively, with no phase object in the beam. FIGS. 6C and 6D represent the intensity pattern at the crossed phase gratings and 15 mm past the crossed phase gratings, respectively, with the star shaped phase object in the beam, as shown in FIG. 7A. Based on the spot patterns in FIGS. 6B and 6D, the local gradients are determined, the phase reconstructed, the amplitude solved for, and the fields at the entrance to the crossed phase gratings determined. The resultant fields are then back-propagated to the location where the phase object was placed in the beam. The two phases are then subtracted and the resultant phase unwrapped using a multigrid algorithm to determine the phase of the object. The results of this phase recovery process are shown in FIG. 7B. FIG. 7C shows an azimuthal lineout at a radius of one fourth the object's diameter for both the actual black line and reconstructed phases dashed gray line in FIGS. 7A and 7B, respectively. This lineout illustrates that the amplitude and spatial frequency of the phase object are quantitatively reproduced. There is a slight high frequency degradation as evidenced by the slope of the edges in the reconstructed phase versus the actual phase, and a low frequency noise term present in the reconstructed phase. The mean error in the full-width at half-maximum and the amplitude between the reconstructed versus applied phase bars shown in FIG. 7C was 13 and 0.4%, respectively.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

I claim:

1. A method for producing a simulated reconstructed x-ray wavefront, comprising:
    propagating a first x-ray wavefront along an optical path defined from an x-ray source through a wavefront sensor element to a detector, wherein said detector detects a reference wavefront;
    inserting a sample into said optical path between said x-ray source and said wavefront sensor;
    propagating a second x-ray wavefront along said optical path and to said detector, wherein said detector detects a signal wavefront;
    calculating a phase gradient between said reference wavefront and said signal wavefront;
    simulating the propagation of said signal wavefront back to a simulated screen located at the position of said sample to produce a propagated wavefront;
    adjusting said propagated wavefront with a percentage of said phase gradient to produce an adjusted wavefront;
    simulating the propagation of said adjusted wavefront to said detector to produce a simulated signal wavefront;
    calculating a subsequent phase gradient between said signal wavefront and said simulated signal wavefront;
    simulating the propagation of said simulated signal wavefront back to said simulated screen to produce a second propagated wavefront;
    adjusting said second propagated wavefront with a percentage of said subsequent phase gradient to produce a second adjusted wavefront;
    simulating the propagation of said second adjusted wavefront to said detector to produce a reconstructed x-ray wavefront; and
    displaying said reconstructed x-ray wavefront.

2. The method of claim 1, further comprising providing said first x-ray wavefront and said second x-ray wavefront from a source selected from the group consisting of a free-electron laser, an x-ray tube, a laser-produced source, an x-pinch source, a synchrotron and a micro-focus tube.

3. The method of claim 1, wherein said second x-ray wavefront comprises an energy within a range from about 100 eV to about 60 KeV.

4. The method of claim 1, wherein said first x-ray wavefront and said second x-ray wavefront comprise a cross-sectional area that propagates according to a characterization selected from the group consisting of collimated, diverging and converging.

5. The method of claim 1, wherein said wavefront sensor element comprises a Hartmann plate.

6. The method of claim 1, wherein said wavefront sensor comprises a zone plate array.

7. The method of claim 1, wherein said wavefront sensor element comprises crossed phase gratings.

8. The method of claim 7, wherein said crossed phase gratings comprises first portions having a first index of refraction at the wavelength of said first x-ray wavefront and said second x-ray wavefront and wherein said crossed phase gratings comprise second portions having a second index of refraction at the wavelength of said first x-ray wavefront and said second x-ray wavefront, wherein said first index and said second index are different.

9. The method of claim 1, wherein said detector is selected from the group consisting of a CCD camera, a scintillator, at least one phosphor screen, at least one imaging plate, an x-ray film and amorphous selenium.

10. The method of claim 1, wherein said first detector is located at a distance d from said wavefront sensor, wherein said distance is selected from the group consisting of (i) between 0 and $d^2/\lambda$; (ii) between $d^2/\lambda$ and $2d^2/\lambda$, where $\lambda$ is the wavelength of the x-rays of said x-ray wavefront and (iii) multiples of these distances.

11. The method of claim 1, further comprising measuring the intensity of said signal wavefront.

12. The method of claim 1, wherein said first x-ray wavefront and said second x-ray wavefront are propagated from a backlighter selected from the group consisting of a spatially coherent backlighter and a periodic backlighter.

13. The method of claim 1, further comprising:
    calculating 1 to n subsequent phase gradients between said signal wavefront and 1 to n reconstructed x-ray wavefronts, where n is the number of iterations;
    simulating the propagation of said 1 to n reconstructed x-ray wavefronts back to said simulated screen to produce 1 to n propagated wavefronts;
    adjusting said 1 to n propagated wavefronts with a percentage of said 1 to n subsequent phase gradients to produce a 1 to n adjusted wavefronts; and
    simulating the propagation of said 1 to n adjusted wavefronts to said detector to produce a final reconstructed x-ray wavefront determined, to have a desired phase gradient value.

14. An apparatus for producing a simulated reconstructed x-ray wavefront, comprising:
    an x-ray source or providing at least one of a first x-ray wavefront and a second x-ray wavefront;
    wavefront sensor element;
    a detector;
    wherein said x-ray source, said wavefront sensor element and said detector are aligned on an optical path defined from said x-ray source through said wavefront sensor element to said detector; and
    a computer system comprises a processor and display, wherein said processor comprises an algorithm for carrying out a series of steps comprising:
    calculating a phase gradient between a reference wavefront and a signal wavefront;
    simulating the propagation of said signal wavefront hack to a simulated screen located, at the position of said sample to produce a propagated wavefront;
    adjusting said propagated wavefront with a percentage of said phase gradient to produce an adjusted wavefront;
    simulating the propagation of said adjusted wavefront to said detector to produce a simulated signal wavefront;
    calculating a subsequent phase gradient between said signal wavefront and said simulated signal wavefront;

simulating the propagation of said simulated signal wavefront back to said simulated screen to produce a second propagated wavefront;

adjusting said second propagated wavefront with a percentage of said subsequent phase gradient to produce a second adjusted wavefront; and simulating the propagation of said second adjusted wavefront to said detector to produce a reconstructed x-ray wavefront.

15. The apparatus of claim 14, wherein said source is selected from the group consisting of a free-electron laser, an x-ray tube, a laser-produced source, an x-pinch source, a synchrotron and a micro-focus tube.

16. The apparatus of claim 14, wherein said source is capable of producing an x-ray wavefront having an energy within a range from about 100 eV to about 60 KeV.

17. The apparatus of claim 14, wherein said source is capable of producing an x-ray wavefront having a cross-sectional area selected from the group consisting of collimated, diverging and converging.

18. The apparatus of claim 14, wherein said wavefront sensor element comprises a Hartmann plate.

19. The apparatus of claim 14, wherein said wavefront sensor element comprises a one plate array.

20. The apparatus of claim 14, wherein said wavefront sensor element comprises a crossed phase grating.

21. The apparatus of claim 20, wherein said crossed phase grating comprises first portions having a first index of refraction at the wavelength of said first x-ray wavefront and said second x-ray wavefront and wherein said crossed phase grating comprises second portions having a second index of refraction at the wavelength of said first x-ray wavefront and said second x-ray wavefront, wherein said first index and said second index are different.

22. The apparatus of claim 14, wherein said detector is selected from the group consisting of a CCD camera, a scintillator, at least one phosphor screen, at least one imaging plate, an x-ray film and amorphous selenium.

23. The apparatus of claim 14, wherein said detector is placed at a distance d from said wavefront sensor element, wherein said distance is selected from the group consisting of (i) between 0 and $d^2/\lambda$ and (ii) between $d^2/\lambda$ and $2d^2/\lambda$, where $\lambda$ is the wavelength of the x-rays of said x-ray wavefront and (iii) multiples of these distances.

24. The apparatus of claim 14, further comprising means for calculating the intensity of said signal wavefront.

25. The apparatus of claim 14, further comprising a backlighter positioned between said source and said wavefront sensor element, wherein said backlighter is selected from the group consisting of a spatially coherent backlighter or a periodic backlighter.

26. The apparatus of claim 14, wherein said algorithm further comprises the steps of:

calculating 1 to n subsequent phase gradients between said signal wavefront and 1 to n reconstructed x-ray wavefronts, where n is the number of iterations;

simulating the propagation of said 1 to n reconstructed x-ray wavefronts back to said simulated screen to produce 1 to n propagated wavefronts;

adjusting said 1 to n propagated wavefronts with a percentage of said 1 to n subsequent phase gradients to produce a 1 to n adjusted wavefronts; and simulating the propagation of said 1 to n adjusted wavefronts to said detector to produce a final reconstructed x-ray wavefront determined to have a desired phase gradient value.

* * * * *